United States Patent
Snopek et al.

(10) Patent No.: US 11,593,710 B1
(45) Date of Patent: Feb. 28, 2023

(54) METHODS AND SYSTEM TO ESTIMATE RETAIL PRESCRIPTION WAITING TIME

(71) Applicant: WALGREEN CO., Deerfield, IL (US)

(72) Inventors: Adam Robert Snopek, Chicago, IL (US); Lawrence Hernandez Salud, Chicago, IL (US); Nicholas Phillip Baldwin, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 598 days.

(21) Appl. No.: 16/714,269

(22) Filed: Dec. 13, 2019

(51) Int. Cl.
*G06Q 10/08* (2012.01)
*G06N 20/00* (2019.01)
*G16H 20/10* (2018.01)
*G06Q 10/087* (2023.01)
*G06Q 10/04* (2023.01)

(52) U.S. Cl.
CPC ............ *G06N 20/00* (2019.01); *G06Q 10/04* (2013.01); *G06Q 10/087* (2013.01); *G16H 20/10* (2018.01)

(58) Field of Classification Search
CPC ........ G06N 20/00; G16H 20/10; G16H 50/30; G16H 50/20; G16H 10/60; G16H 30/40; G16H 40/20; G16H 50/50; G16H 10/20; G16H 20/30; G16H 15/00; G16H 40/63; G16H 40/67; G06Q 10/04; G06Q 10/087
See application file for complete search history.

(56) References Cited

U.S. PATENT DOCUMENTS

| | | | | |
|---|---|---|---|---|
| 2005/0228766 | A1* | 10/2005 | Roberts | G06Q 10/10 |
| 2006/0010009 | A1* | 1/2006 | Fangman | G16H 70/40 |
| | | | | 705/2 |
| 2007/0136376 | A1* | 6/2007 | Kusakabe | G16H 10/60 |

(Continued)

OTHER PUBLICATIONS

Kelly et al., "The Last Mile: Operationalizing Data Science", Pivotal Software, Inc., 2017, https://content.pivotal.io/white-papers/the-last-mile-operationalizing-data-science, 12 pages.
(Continued)

*Primary Examiner* — Chris Parry
*Assistant Examiner* — Hassan A Khan
(74) *Attorney, Agent, or Firm* — Marshall, Gerstein & Borun LLP; Randall G. Rueth (57) ABSTRACT

Example methods, apparatus, and articles of manufacture to estimate waiting times of prescriptions are disclosed herein. An example computer-implemented method, executed by a processor, to estimate a waiting time of a prescription for a medication includes training a machine learning model using, for each of a plurality of previously filled prescriptions, a set of characteristics of the previously filled prescription, and a fill time for the previously filled prescription, receiving a prescription for a medication for a patient, receiving a request for an estimated waiting time for filling the prescription medication for the patient, identifying a set of characteristics of the prescription medication for the patient, applying the set of characteristics of the prescription medication to the machine learning model to determine the estimated waiting time for filling the prescription medication (Continued)

for the patient, and providing an indication of the estimated waiting time for display on a client device.

18 Claims, 7 Drawing Sheets

(56) References Cited

U.S. PATENT DOCUMENTS

| | | | | |
|---|---|---|---|---|
| 2009/0012813 | A1* | 1/2009 | Berzansky | G16H 20/13 705/2 |
| 2010/0008255 | A1* | 1/2010 | Khosravy | H04W 4/21 370/254 |
| 2013/0252591 | A1* | 9/2013 | Sasaki | H04M 1/72451 455/414.1 |
| 2013/0304534 | A1* | 11/2013 | Mehta | G06Q 10/1095 705/7.19 |
| 2013/0339048 | A1* | 12/2013 | Roberts | G16H 20/10 705/2 |
| 2014/0074743 | A1* | 3/2014 | Rademaker | G06Q 30/0601 705/334 |
| 2014/0278466 | A1* | 9/2014 | Simmons | G16H 20/10 705/2 |
| 2015/0058035 | A1* | 2/2015 | Ayshford | G16H 40/20 705/2 |
| 2015/0127401 | A1* | 5/2015 | Hogg | G06Q 30/0281 705/7.15 |
| 2015/0242592 | A1* | 8/2015 | Weiss | G16H 20/10 705/2 |
| 2016/0055319 | A1* | 2/2016 | Ikegaya | G16H 20/60 705/3 |
| 2016/0148167 | A1* | 5/2016 | Li | G06Q 10/1095 705/7.19 |
| 2017/0076058 | A1* | 3/2017 | Stong | G16H 20/10 |
| 2017/0161442 | A1* | 6/2017 | Runci | G16H 40/20 |
| 2018/0240539 | A1* | 8/2018 | Doherty | G16H 20/10 |
| 2019/0304596 | A1* | 10/2019 | Padala | G16H 40/20 |
| 2019/0355481 | A1* | 11/2019 | Lamb | G16H 80/00 |
| 2020/0005409 | A1* | 1/2020 | Rowden | G06Q 50/14 |
| 2020/0050949 | A1* | 2/2020 | Sundararaman | G06F 40/284 |
| 2020/0066397 | A1* | 2/2020 | Rai | G06Q 10/067 |
| 2020/0135317 | A1* | 4/2020 | Karbowicz | G16H 20/10 |
| 2020/0402648 | A1* | 12/2020 | Ghosh | G16H 20/10 |
| 2021/0096567 | A1* | 4/2021 | Ziniti | G05D 1/0212 |

OTHER PUBLICATIONS

Microsoft Docs, "Mining Structures (Analysis Services—Data Mining", Microsoft, 2018, https://docs.microsoft.com/en-us/sql/analysis-services/data-mining/mining-structures-analysis-services-data-mining?view=sql-server2017, as downloaded on Sep. 5, 2019, 8 pages.
U.S. Appl. No. 16/521,290, filed Jul. 24, 2019.

* cited by examiner

METHODS AND SYSTEM TO ESTIMATE RETAIL PRESCRIPTION WAITING TIME

FIELD OF THE DISCLOSURE

This disclosure relates generally to retail prescriptions, and, more particularly, to estimating and reducing patient waiting time for retail prescriptions to be filled.

BACKGROUND

In a competitive marketplace, patient satisfaction is especially important. Patient satisfaction with a retail pharmacy has been correlated to the amount of time it takes to fill a prescription as well as patient perception of that time. Retail pharmacies have already reduced perceived prescription fill time by offering multiple channels of ordering a prescription such as by ordering a prescription by mobile application, by fax, or by an electronic prescription connection with the prescribing medical personnel. However, there are remaining delays involving contacting the prescriber for a new prescription or contacting the prescriber as part of insurance company prescription "prior authorization" procedure. There is also perceived wait time. Among the most important ways to decrease perceived wait time and increase patient satisfaction is to accurately determine and inform the patient in advance of how long the prescription will take to fill. This allows the patient the choice of waiting at the pharmacy counter for a few minutes if the prescription will be filled quickly, staying in the store to do additional shopping, or to going to another location if an affiliated store has the medication available more quickly.

However, prediction of fill times can be challenging as there is no single time that can be accurately applied to all patients. A prescription fill time is often dependent upon insurance which may delay or deny the fill or require a "prior authorization", also referred to as with "pre authorization" in this document, which is a confirmation of the insurance company payment which requires contacting the prescriber. Other factors such as the medicine being in-stock, the number of other patients waiting, the number of prescriptions waiting to be filled, the time of day and the number and type of employees (pharmacists, assistants, clerks) on duty are likely to influence the waiting time. What is needed is a better way to reduce prescription fill time and also to accurately predict in advance the amount of time it takes to fill a retail prescription.

SUMMARY

To provide a patient with an estimated waiting time (also referred to herein as a "fill time") for the pharmacy to fill a prescription for the patient, a prescription waiting time estimation system may be trained using various machine learning techniques to create a machine learning model for estimating the waiting time based on prescription characteristics. The prescription waiting time estimation system may be trained by obtaining previously filled prescriptions and identifying a set of characteristics for each of the previously filled prescriptions as well as actual fill times for each of the previously filled prescriptions. The set of characteristics for a previously filled prescription may include medication and usage information included in the prescription such as a medical diagnosis associated with the prescription, the prescription dosage, the days' supply, the amount of medication per dose, the drug type, the drug class and/or subclass, the drug name, the dosage form, prescriber instructions (e.g., take one dose two times daily), a number of refills remaining, whether prior authorization is required and/or has been obtained. The set of characteristics for a previously filled prescription may also include payor information indicative of the person or entity responsible for purchasing the prescription such as a name or identifier of the payor, a name or identifier of the patient's insurance plan, fees associated with the payor, benefits information, etc. Additionally, the set of characteristics for a previously filled prescription may include prescriber information such as a name or identifier of the prescriber, the type of prescriber, etc., and patient information such as the age of the patient, demographic information for the patient, socioeconomic data for the patient, health indicators for the patient, the patient zip code, etc. Furthermore, the set of characteristics for a previously filled prescription may include retail pharmacy information for the retail pharmacy filling the prescription such as the number of pharmacists or pharmacy technicians currently on duty, pharmacy stock information indicating the medications currently in supply at the pharmacy and the amount of supply for each medication, the number of prescriptions currently waiting to be filled, store hours, etc., and geographic information for the retail pharmacy filling the prescription.

The prescription waiting time estimation system may obtain these characteristics from the retail pharmacy that previously filled the prescription. For example, when a retail pharmacy fills a prescription, a workstation at the retail pharmacy may provide these characteristics to the prescription waiting time estimation system. The set of characteristics and fill time for each previously filled prescription may be analyzed using the various machine learning techniques to generate the machine learning model for estimating a waiting time for filling a subsequent prescription.

After the training period, the prescription waiting time estimation system may receive a prescription for a medication for a patient. The prescription waiting time estimation system may receive the prescription from the prescriber, via an image of the prescription captured by the patient at the patient's client device, or from pharmacy personnel who may enter the prescription information at a pharmacy workstation which transmits the prescription information to the prescription waiting time estimation system. The patient, the prescriber, or pharmacy personnel may designate a retail pharmacy location for filling the prescription. The prescription waiting time estimation system may then identify prescription characteristics for the prescription including medication and usage information, payor information, prescriber information, patient information, retail pharmacy information, and geographic information for the retail pharmacy.

The prescription waiting time estimation system may obtain these prescription characteristics from the prescription, from a prescriber database storing prescriber information for several prescribers, from a patient database storing patient information for several patients such as a user profile, from a payor database storing payor information for several payors, from a retail pharmacy database storing retail pharmacy information for several retail pharmacy, and/or from computing devices at retail pharmacy locations such as a retail pharmacy location which may include real-time or at least near real-time information about the number of pharmacists or pharmacy technicians on duty, the number of prescriptions currently waiting to be filled at the retail pharmacy location, amounts of medicines currently in stock, etc.

Then the prescription waiting time estimation system may apply the prescription characteristics for the prescription to the machine learning model to estimate the waiting time for filling the prescription. The estimated waiting time may then be provided to the patient's client device or to a pharmacy workstation of a retail pharmacy filling the prescription for display to the patient or pharmacy personnel.

In some embodiments, the prescription waiting time estimation system may identify alternative retail pharmacies located within a threshold distance of the retail pharmacy. The prescription waiting time estimation system may obtain retail pharmacy information for each of the alternative retail pharmacies and apply the obtained retail pharmacy information to the machine learning model to determine whether the estimated waiting time is shorter at any of the alternative retail pharmacies. If the estimated waiting time is shorter at an alternative retail pharmacy, the prescription waiting time estimation system may provide an indication of the alternative retail pharmacy and a recommendation for the patient to have the prescription filled at the alternative retail pharmacy to the patient's client device or to a pharmacy workstation of the retail pharmacy filling the prescription for display to the patient or pharmacy personnel.

In an embodiment, a computer-implemented method for estimating the waiting time for a prescription to be filled is provided. The method includes training a machine learning model using, for each of a plurality of previously filled prescriptions, a set of characteristics of the previously filled prescription, and a fill time for the previously filled prescription. The method further includes receiving a prescription for a medication for a patient, receiving a request for an estimated waiting time for filling the prescription medication for the patient, and identifying a set of characteristics of the prescription medication for the patient. Moreover, the method includes applying the set of characteristics of the prescription medication to the machine learning model to determine the estimated waiting time for filling the prescription medication for the patient, and providing an indication of the estimated waiting time for display on a client device.

In another embodiment, a non-transitory computer-readable storage medium having instruction is included. The instructions, when executed by a processor, cause the processor to train a machine learning model using, for each of a plurality of previously filled prescriptions, (i) a set of characteristics of the previously filled prescription, and (ii) a fill time for the previously filled prescription. The instructions further cause the processor to receive a prescription for a medication for a patient, receive a request for an estimated waiting time for filling the prescription medication for the patient, and identify a set of characteristics of the prescription medication for the patient. Furthermore, the instructions cause the processor to apply the set of characteristics of the prescription medication to the machine learning model to determine the estimated waiting time for filling the prescription medication for the patient, and provide an indication of the estimated waiting time for display on a client device.

The figures depict embodiments of this disclosure for purposes of illustration only. One skilled in the art will readily recognize from the following discussion that alternate embodiments of the structures and methods illustrated herein may be employed without departing from the principles set forth herein.

In general, the same reference numbers will be used throughout the drawing(s) and accompanying written description to refer to the same or like parts. The figures are not to scale. Connecting lines or connectors shown in the various figures presented are intended to represent example functional relationships and/or physical or logical couplings between the various elements.

DETAILED DESCRIPTION

To overcome these and/or other problems, methods, apparatus, and articles of manufacture to estimate wait time for retail prescriptions are disclosed herein. In disclosed examples, estimated waiting times of prescriptions are provided to patients, pharmacy personnel, and/or prescribers before they are filled. A patient is, thus, provided with additional information she may need to determine whether she will wait in the store, come back later, or enquire about wait times at other affiliated stores. While the examples disclosed herein are described with reference to medications, aspects of this disclosure can be used to estimate waiting times for other goods requiring a prescription (e.g., therapy, medical tests, medical procedures, medical supplies, etc.).

Reference will now be made in detail to non-limiting examples, some of which are illustrated in the accompanying drawings.

Figure 1:
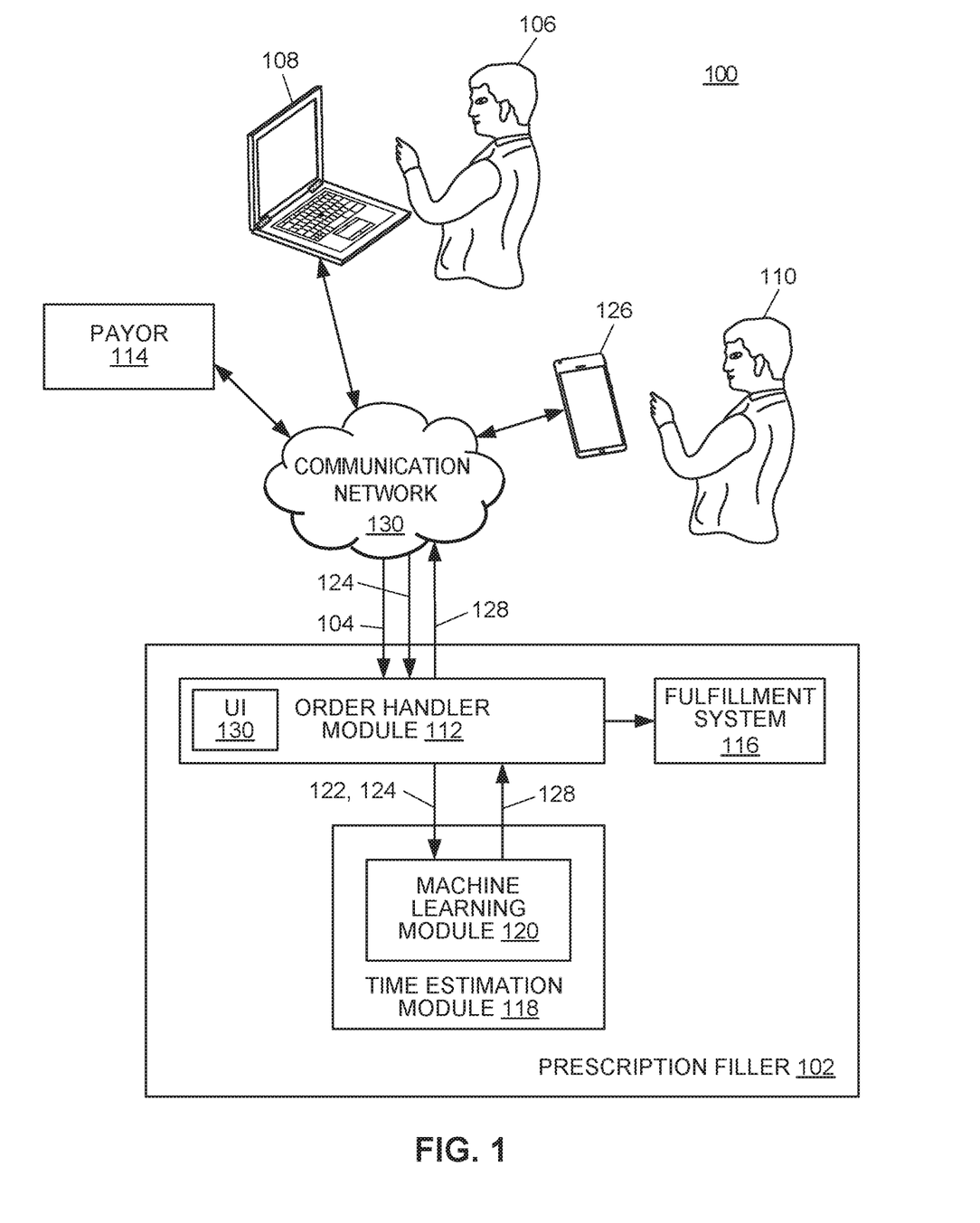
FIG. 1 is a block diagram of an example system to estimate waiting times of prescriptions, in accordance with teachings of this disclosure.

FIG. 1 is a diagram of an example system 100 to, among possibly other things, estimate waiting times of prescriptions for medications. The system 100 includes a prescription filler 102 (e.g., a pharmacy, etc.) to fill prescriptions 104 for medications. The prescriptions 104 may be received from any number or type(s) of prescriber (e.g., a medical professional, a doctor, a nurse practitioner, a dentist, etc.) or representatives thereof, one of which is designated at reference numeral 106, via any number or type(s) of user devices (e.g., a facsimile, a laptop computer, a tablet, a smartphone, etc.), one of which is designated at reference numeral 108. While not shown in FIG. 1, prescriptions 104 may additionally, or alternatively, be electronically sent to the prescription filler 102 via the patient's client device, physically mailed or faxed to, or physically dropped off at the prescription filler 102 by the prescriber 106 (or a representative thereof) or by a patient 110.

An order handler module 112 of the prescription filler 102 processes the prescription(s) 104 for the patient 110 by submitting orders for the prescriptions 104 to the payor(s)

associated with patient 110 (one of which is designated at reference numeral 114). The payor may be an individual or the organization, such as an insurance company, paying for the prescription. The prescription(s) 104 approved by the payor 114 are sent to a fulfillment system 116 to prepare the prescription(s) 104 for delivery to the patient 110. Otherwise, the prescription(s) 104 are routed for manual handling and processing.

To estimate the waiting times of prescriptions (e.g., the estimated waiting time to fill a quantity of medication prescribed), the prescription filler 102 includes a waiting time estimation module 118. The waiting time estimation module 118 may be, or include a portion of a memory unit (e.g., the program memory 602 of FIG. 6) configured to store software, and machine- or computer-readable instructions that, when executed by a processing unit (e.g., the processor 604 of FIG. 6), cause the waiting time estimation module 118 to estimate prescription waiting times in view of a patient's coverage(s), the medication and quantity prescribed, the prescriber information, store information, etc. In some examples, prescription waiting times are also estimated in view of ancillary information such as, but not limited to, demographic information, socioeconomic information, geographic information, etc. The estimation may be for the time at the current pharmacy, or for a neighboring pharmacy if the estimated wait time is unacceptable to the patient.

In the illustrated example of FIG. 1, the waiting time estimation module 118 estimates prescription waiting times using a machine learning module 120. Prescription information (e.g., medication, quantity, prescription instruction(s), coverage information (e.g. if insurance coverage requires prior authorization from the prescriber prior to dispensing the medication) ancillary information, store information including pharmacists and other employees currently on duty, time of day, prescriber information, prescriptions waiting to fill, patients currently waiting, etc.) are input to the machine learning module 120. The machine learning module 120 may be, or include a portion of a memory unit (e.g., the program memory 602 of FIG. 6) configured to store software, and machine- or computer-readable instructions that, when executed by a processing unit (e.g., the processor 604 of FIG. 6), cause the machine learning module 120 to executed a machine learning model to estimate prescription waiting times. In some examples, the machine learning module 120 implements gradient boosting machine learning, for example, using the open source extreme gradient boosting (xgboost)) algorithm.

More specifically, the machine learning module 120 generates the machine learning model based on training data from previously filled prescriptions. The training data may include, for each previously filled prescriptions, a set of characteristics of the previously filled prescription such as the characteristics described above, and an actual fill time for the previously filled prescription. The machine learning module 120 may classify the data for each previously filled prescription into one of several subsets of training data, where each subset corresponds to a different fill time (e.g., one hour) or range of fill times (e.g., between one and three hours). The machine learning module 120 may then analyze each of the subsets to generate the machine learning model for estimating prescription waiting times. Techniques for generating the machine learning model may include, gradient boosting, neural networks, deep learning, linear regression, polynomial regression, logistic regression, support vector machines, decision trees, random forests, nearest neighbors, or any other suitable machine learning technique.

For example, when the machine learning technique is random forests, the machine learning module 120 may collect several representative samples of each of the subsets of the training data. Using each representative sample, the machine learning module 120 may generate a decision tree for estimating a prescription waiting time. The machine learning module 120 may then aggregate and/or combine each of the decision trees to generate the machine learning model, by for example averaging the prescription waiting times determined at each individual tree, calculating a weighted average, taking a majority vote, etc. In some embodiments, the machine learning module 120 may also generate decision trees when the machine learning technique is boosting.

Each decision tree may include several nodes, branches, and leaves, where each node of the decision tree represents a test on a prescription characteristic (e.g., are there more than two prescriptions waiting to be filled at the retail pharmacy)?). Each branch represents the outcome of the test (e.g., there are more than two prescriptions waiting to be filled). Moreover, each leaf represents a different prescription waiting time (e.g., one hour), confidence interval (e.g., 0.9-4.2 hours with 95 percent confidence), or likelihood based on the combined test outcomes for the branches which connect to the leaf.

For example, the machine learning module 120 may generate a decision tree where a first node corresponds to whether the prescription quantity is greater than 60. If the prescription quantity is less than 60, a first branch may connect to a first leaf node which may indicate that the waiting time will be between one and three hours with 75 percent confidence. If the prescription quantity is not less than 60, a second branch may connect to a second node which corresponds to whether prior authorization is required.

If prior authorization is not required, a third branch may connect to a second leaf node which may indicate that the repair time will be between five and seven hours with 85 percent confidence. However, if prior authorization is required, a fourth branch may connect to a third leaf node which may indicate that the repair time will be between 24 and 36 hours with 95 percent confidence. While the decision tree includes three leaf nodes and four branches, this is merely an example for ease of illustration only. Each decision tree may include any number of nodes, branches, and leaves, having any suitable number and/or types of tests on prescription characteristics and/or statistical measures.

In other embodiments, the machine learning technique used by the machine learning module 120 may be a regression analysis, such as logistic regression, linear regression, polynomial regression, etc. For example, in a linear regression, the actual fill times may be dependent variables and each of the prescription characteristics may be independent variables. The machine learning module 120 may generate a machine learning model as an equation which most closely approximates the actual fill times from the prescription characteristics. In some embodiments, an ordinary least squares method may be used to minimize the difference between the value of predicted waiting times using the machine learning model and the actual fill times. Additionally, the differences between the values of each predicted waiting time ($\hat{y}_i$) using the machine learning model and actual fill time ($\hat{y}_i$) may be aggregated and/or combined in any suitable manner to determine a mean square error (MSE) of the regression. The MSE may then be used to determine a standard error or standard deviation ($\sigma_\varepsilon$) in the machine learning model, which may in turn be used to create confidence intervals. For example, assuming the data is normally distributed, a confidence interval which includes about three standard deviations from the predicted waiting time using the machine learning model ($\hat{y}_i-3\sigma_\varepsilon-\hat{y}_i+3\sigma_\varepsilon$) may correspond to 99.5 percent confidence. A confidence interval which includes about two standard deviations from the predicted waiting time using the machine learning model ($\hat{y}_i-2\sigma_\varepsilon=\hat{y}_i+2\sigma_\varepsilon$) may correspond to 95 percent confidence. Moreover, a confidence interval which includes about 1.5 standard deviations from the predicted waiting time using the machine learning model ($\hat{y}_i-1.5\sigma_\varepsilon-\hat{y}_i+1.5\sigma_\varepsilon$) may correspond to 90 percent confidence.

The machine learning module 120 may then test the machine learning model generated using gradient boosting, neural networks, deep learning, linear regression, polynomial regression, support vector machines, decision trees, random forests, nearest neighbors, or any other suitable machine learning technique. For example, the machine learning module 120 may obtain test data including test prescription characteristics and a test waiting time. While the test waiting time is known (e.g., the test prescription characteristics and test waiting time are also from a previously filled prescription similar to the training data but the test prescription characteristics and test waiting time are used for testing purposes), the machine learning module 120 may determine the waiting time by applying the test prescription characteristics to the machine learning model.

For example, when the machine learning model is a random forest, the machine learning module 120 may traverse nodes from the aggregated and/or combined decision trees using the test prescription characteristics. The waiting time determined by the machine learning module 120 may then be compared to the test waiting time. In some embodiments, if the waiting determined by the machine learning module 120 is within a threshold amount (e.g., one hour) of the test waiting time, the determination may be determined correct.

In any event, when the machine learning module 120 is correct more than a predetermined threshold amount of the time, the machine learning model may be used for estimating waiting times for prescriptions which have not yet been filled. On the other hand, if the machine learning module 120 is not correct more than the threshold amount, the machine learning module 120 may continue obtaining sets of training data for previously filled prescriptions for further training.

Figure 2:
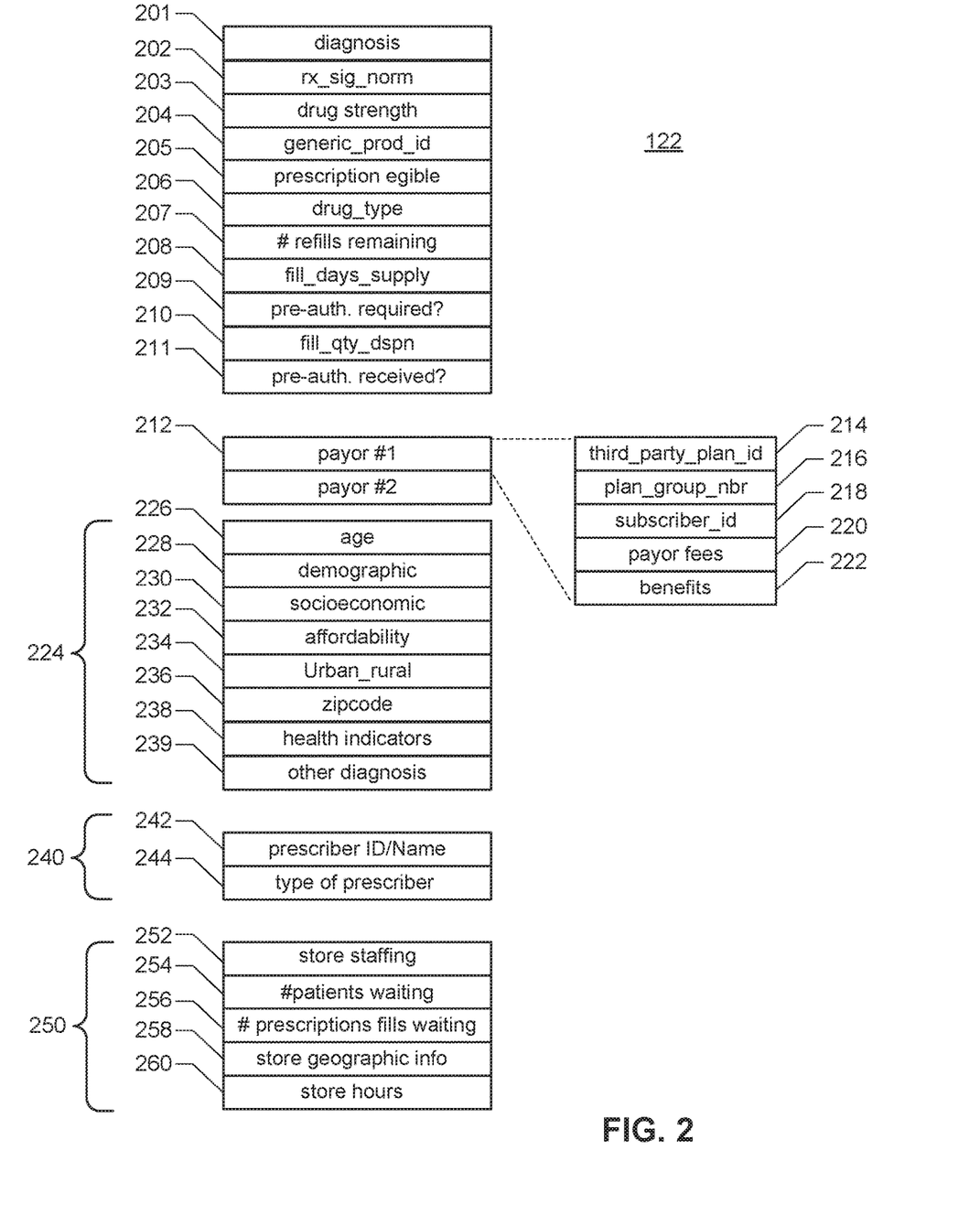
FIG. 2 is a block diagram of an example input vector for the machine learning module of FIG. 1.

When a patient requests an estimated waiting time for a prescription, the machine learning module 120 obtains a set of prescription characteristics for the prescription. The set of prescription characteristics may be used as an input vector to the machine learning module for estimating the waiting time for the prescription. The machine learning module 120 may obtain these prescription characteristics from the prescription, from a prescriber database storing prescriber information for several prescribers, from a patient database storing patient information for several patients such as a user profile, from a payor database storing payor information for several payors, from a retail pharmacy database storing retail pharmacy information for several retail pharmacy, and/or from computing devices at retail pharmacy locations such as a retail pharmacy location which may include real-time or at least near real-time information about the number of pharmacists or pharmacy technicians on duty, the number of prescriptions currently waiting to be filled at the retail pharmacy location, amounts of medicines currently in stock, etc. An example input vector 122 to the machine learning module 120 is shown in FIG. 2. A diagnosis field 201 represents a medical diagnosis associated with the prescription. An rx_sign_norm field 202 represents usage information, i.e., how the medication is to be used (e.g., take 1 dose two times daily), a drug strength field 203 represents an amount of the medication per dose, a generic_prod_id field 204 provides information regarding generic equivalents, and a drug_type field 206 includes 14 characters that indicate drug group (e.g., decongestant), drug class (e.g., sympathomimetics), drug subclass (e.g., systemic decongestants), drug name (e.g., pseudoephedrine), drug name ext. (e.g., hydrochloride), dosage form (e.g., tablet) and strength (e.g., 60 mg). The input vector 122 further includes the number of refills remaining 207, whether prior authorization (referred to as pre-auth in FIG. 2o) is required 209, whether prior authorization has already been obtained 211, a fill_days_supply field 208 that indicates how many days are being supplied, and a fill_qty_dspn field 210 that indicates how many are being dispensed, as well as payor information 212 for one or more payors which includes a third_party_plan_id field 214 that represents the payor, a plan_group_nbr field 216 that identifies a patient's plan, and a subscriber_id field 218 that identifies an insured of the plan. Fees associated with the payor are stored in a fees field 220, and a benefits field 222 contains benefits information. In some examples, the input vector 122 includes ancillary information 224 such as an age field 226, a demographic field 228, a socioeconomic field 230, an affordability field 232, an urban/rural field 234, a zipcode field 236, a health indicators field 238 (e.g., storing smoking information), and another diagnosis field 239. In addition, information about the prescriber is included such as the name or id 242 and the type of prescriber 244 (such as surgeon, pediatrician, internist, nurse practitioner pediatrician). Particular store information may also be included such as the number of pharmacists 240 or pharmacy technicians currently on duty 242, a pharmacy stock indication (to indicate if the medicine is out of stock) 244, the number of prescriptions currently waiting to be filled 246, an indicator that the patient is waiting in the store 248, store hour information such as the closing time 250 or an indication that it is a 24 hour store, or geographic information 252 which might be used to located neighboring stores with a shorter waiting time. While an example machine learning engine input vector 122 is shown in FIG. 2, the fields shown in FIG. 2 may be combined, divided, re-arranged, omitted, eliminated or implemented in any other way. Further, the input vector 122 may include one or more fields, entries, parameters, values in addition to, or instead of those illustrated in FIG. 2, or may include more than one of any or all of the illustrated fields, entries, parameters and values.

Returning to FIG. 1, the waiting time estimation module 118 estimates (e.g., determines, calculates, etc.) prescription waiting times in response to requests 124 for estimated waiting times. Requests 124 for estimated waiting times may be received from, for example, the prescriber 106 (or a representative thereof) via her laptop 108, from the patient 110 via a client device (e.g., a tablet 126), from an employee of the prescription filler 102 (e.g., via a pharmacy workstation), etc. The waiting time estimation module 118 may also provide a proactive push notification of prescription waiting times based on events such as the time of day, etc., to the requesting entity (e.g., the laptop 108 or the tablet 126).

When a request 124 for an estimated waiting time for a prescription 104 is received by the order handler module 112, the request 124 together with an input vector 122 corresponding to the prescription 104 is forwarded to the waiting time estimation module 118. The waiting time estimation module 118 passes the input vector 122 through the machine learning module 120, which estimates a waiting time 128 for the prescription 104. The estimated waiting time 128 is provided to the order handler module 112, which provides the estimated waiting time 128 to the requesting entity (e.g., the laptop 108 or the tablet 126), where it is presented electronically (e.g., on a display of the patient's client device), orally (e.g., via telephone), via text message, etc. In some examples, a person receiving the estimated waiting time 128 can, in response, indicate whether she wants to wait or come back later. In some examples, when a waiting time estimate is requested, the order handler module 112 additionally identifies nearby locations and estimates associated waiting time(s) for the prescription.

In some examples, the prescription filler 102 (e.g., the order handler module 112) implements a user interface (UI) (e.g., a web-based interface) that can be used to request and obtain estimated waiting times for prescriptions, and to request and obtain estimated waiting time(s) for alternative or similar medication(s).

In some examples, the waiting time estimation module 118 forms the input vector 122 based on the prescription 104. In some examples, the requests 124 for estimated waiting times 128 are routed through another portion or system of the prescription filler 102 outside conventional prescription processing.

The prescription filler 102, the laptop 108, the payor 114, and the tablet 126 may be communicatively coupled via any number or type(s) of communication network(s) 130. The communication network(s) include, but are not limited to, the internet, a local area network (LAN), a metropolitan area network (MAN), a wide area network (WAN), a mobile, a wired network, a Wi-Fi® network, a cellular network, a wireless network, a private network, a virtual private network, etc.

Figure 6:
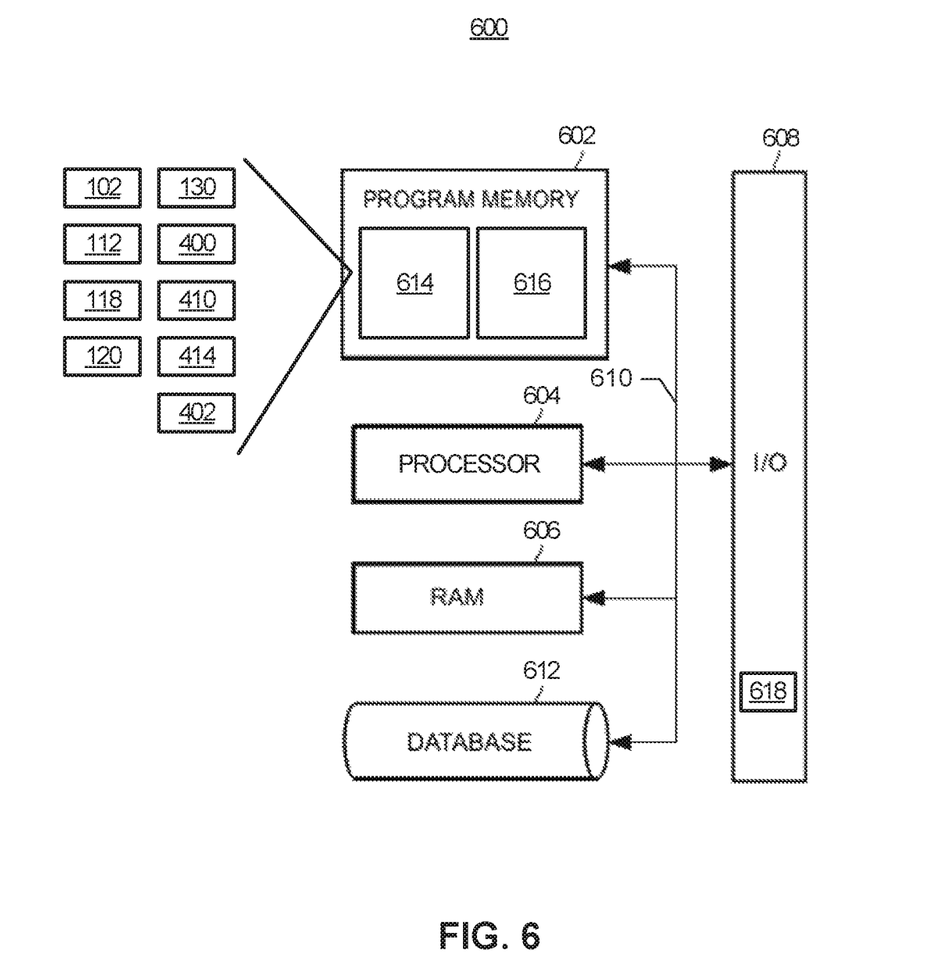
FIG. 6 is a block diagram of an example computing system that may be used to carry out the example processes of FIGS. 3 and 5, in accordance with the described embodiments.

While not shown for clarity of illustration, the prescription filler 102 of FIG. 1 may include various hardware components (e.g., a processor such as the processor 604 of FIG. 6, a server, a workstation, a distributed computing system, a graphics processing unit (GPU), a digital signal processor (DSP), etc.) that may execute software, and machine- or computer-readable instructions to estimate waiting times of prescriptions. The prescription filler 102 also includes data communication components for communicating between devices. Further, one or more of the elements, processes and devices illustrated in FIG. 1 may be combined, divided, re-arranged, omitted, eliminated or implemented in any other way. Further, the prescription filler 102 may include one or more elements, processes or devices in addition to, or instead of, those illustrated in FIG. 1, or may include more than one of any or all of the illustrated elements, processes and devices.

Figure 3:
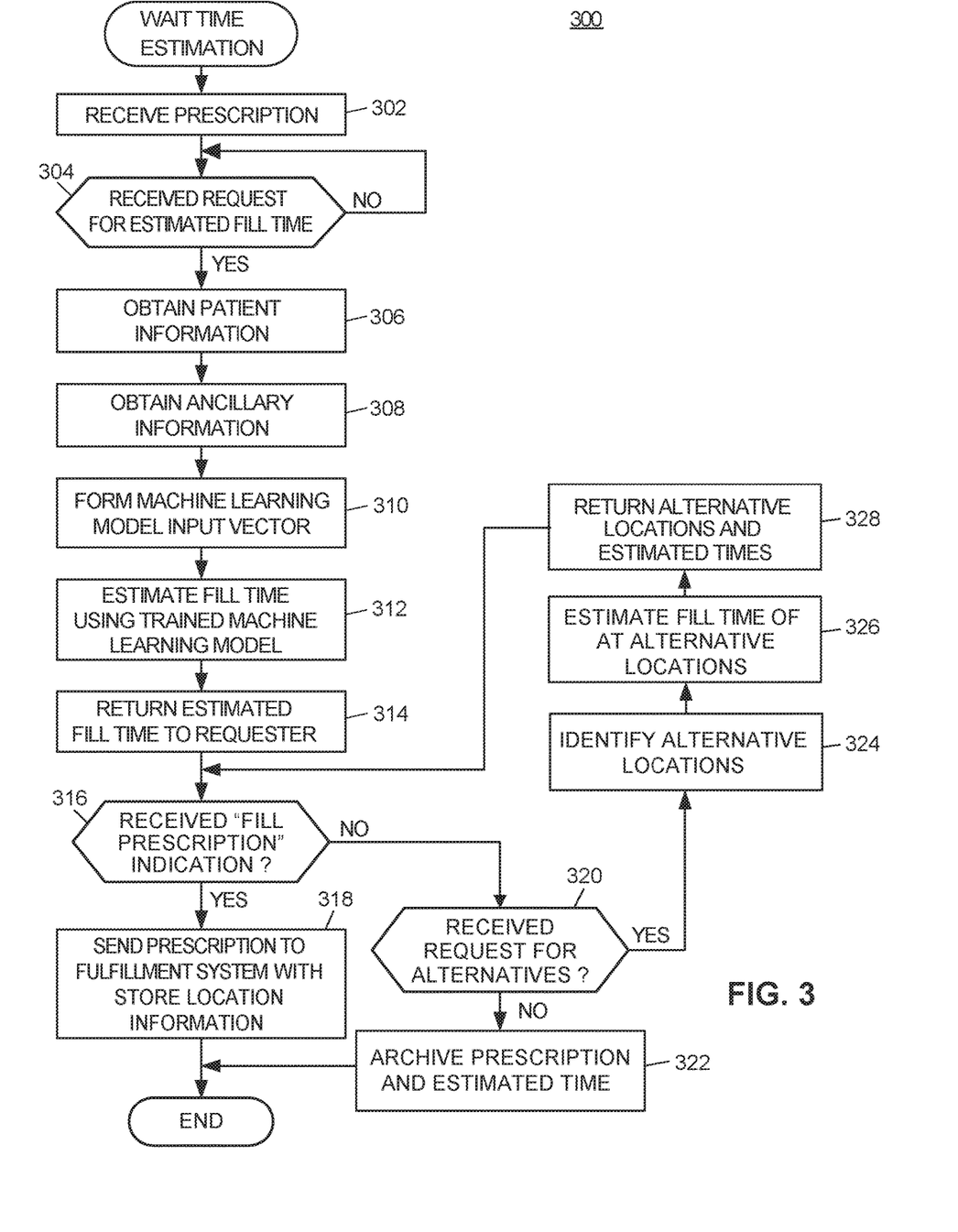
FIG. 3 is a flowchart representative of example methods, hardware logic and instructions for implementing the prescription filler of FIG. 1.

A flowchart 300 representative of example processes, methods, software, firmware, and computer- or machine-readable instructions for implementing the prescription filler 102 is shown in FIG. 3. The processes, methods, software, and machine-readable or computer-readable instructions may be an executable program or portion of an executable program for execution by a processor such as the processor 604 of FIG. 6. The program may be embodied in software or instructions stored on a non-transitory computer- or machine-readable storage medium or disk associated with the processor 604. Further, although the example program is described with reference to the flowchart illustrated in FIG. 3, many other methods of implementing the prescription filler 102 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an application specific integrated circuit (ASIC), a programmable logic device (PLD), a field programmable gate array (FPGA), a field programmable logic device (FPLD), a logic circuit, etc.) structured to perform the corresponding operation without executing software or firmware.

The example process of FIG. 3 begins with the prescription filler 102 receiving a prescription 104 (block 302). If/when a request 124 for an estimated waiting time 128 is received for the prescription 104 from a requester (block 304), patient information including patient demographics 224, payor information 212, 214, 216, 218, 220 and 222 (block 306), and medication order information 201, 202, 203, 204, 206, 207 208 209, 210 and 211 is obtained. Prescriber information 240 is also received from the requester such as the prescriber name or identifier 242 and the type of prescriber 244. Multiple items of store information 250 are also collected such as store staffing information 252, the number of patients waiting 254, the number of prescriptions waiting to be filled 256, store hours 258, and store geographic information 260. Ancillary information 224 may also be obtained (block 308), such as a socioeconomic status 230 for the patient, a health status 238 (e.g., the patient smokes) for the patient, etc. A machine learning input vector 122 is formed from the prescription 104 and the obtained prescription characteristics (block 310), and passed through the machine learning model implemented by the machine learning module 120 (block 312) to obtain a waiting time estimate 128 for the prescription 104. The waiting time estimate 128 is returned to the requester (block 314). If a "fill prescription" indication is received (block 316), the prescription 104 is filled by the fulfillment system 116 (block 318), and control exits from the example process of FIG. 3.

Returning to block 316, if a "fill prescription" indication is not received (block 316), and a request for alternatives is not received (block 320), the prescription 104 and estimated waiting time 128 are stored for subsequent retrieval (block 322), and control exits from the example process of FIG. 3.

Returning to block 320, if a request for alternatives is received (block 320), one or more alternative locations are identified (block 324), and waiting times for the one or more alternative locations are estimated (block 326). The one or more alternative or similar medications and their estimated waiting times are returned to the requester (block 328), and control returns to block 316. In other embodiments, the prescription filler 102 may automatically apply pharmacy information for alternative retail pharmacy locations to the machine learning model to determine whether the estimated waiting time for the prescription is shorter for one or more of the alternative retail pharmacy locations. The prescription filler 102 may identify alternative retail pharmacy locations located within a threshold distance of the selected retail pharmacy location. Then the prescription filler 102 may identify a set of characteristics of each alternative retail pharmacy by obtaining retail pharmacy information for each of the alternative retail pharmacy locations, and apply the obtained retail pharmacy information to the machine learning model to determine whether the estimated waiting time is shorter at any of the alternative retail pharmacies. If the estimated waiting time is shorter at an alternative retail pharmacy, the prescription filler 102 may provide an indication of the alternative retail pharmacy and a recommendation for the patient to have the prescription filled at the alternative retail pharmacy to the patient's client device or to a pharmacy workstation of the retail pharmacy filling the prescription for display to the patient or pharmacy personnel.

Also in some embodiments, the prescription filler 102 may determine whether contacting the prescriber may reduce the estimated waiting time for filling the prescription. For example, one of the prescription characteristics may include whether the prescriber has been contacted. The prescription filler 102 may apply the prescription characteristics including that the prescriber has not been contacted to the machine learning model in a first instance, and may apply the prescription characteristics including that the prescribed has been contacted to the machine learning model in a second instance. The prescription filler 102 may then compare the estimated waiting times in both instances. If the estimated waiting time for the second instance is more than a threshold amount shorter than the estimated waiting time in the first instance, the prescription filler 102 may provide a recommendation to the patient's client device for the patient to contact the prescriber. The recommendation may include an estimated amount of waiting time saved by contacting the prescriber. In other embodiments, the prescription filler 102 may automatically attempt to contact the prescriber, via phone call, email, text message, etc. In yet other embodiments, the prescription filler 102 may automatically attempt to contact the prescriber when the estimated waiting time for the prescription has passed.

Figure 4:
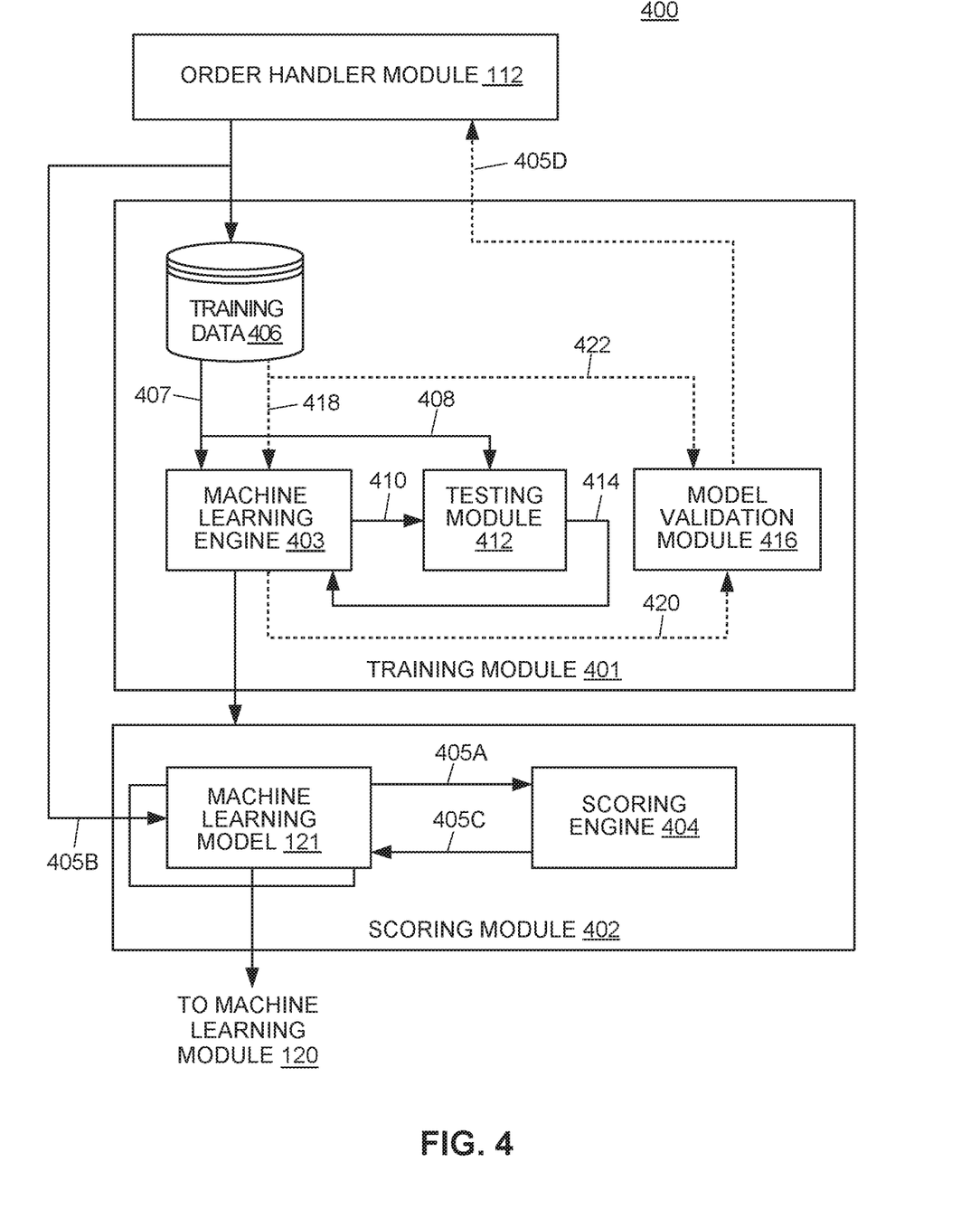
FIG. 4 is a block diagram of an example machine learning training module to train the machine learning module of FIG. 1, in accordance with teachings of this disclosure.

FIG. 4 is a block diagram of an example machine learning training module 400 having a training module 401 and a scoring module 402. The training module 401 includes a machine learning engine 403 for training a machine learning module. The scoring module 402 scores a final machine leaning model 121. Both the training module 401 and the scoring module 402 can be executed for use as the machine learning module 120 of FIG. 1. There can be one or more machine learning models 121 for scoring within the scoring module 402. The training module 401 and the scoring module 402 may be, or include a portion of a memory unit (e.g., the program memory 602 of FIG. 6) configured to store software, and machine- or computer-readable instructions that, when executed by a processing unit (e.g., the processor 604 of FIG. 6), cause the training module 401 to train, test and validate a machine learning model 121 from the machine learning engine 403, and cause the scoring module 402 to provide the waiting time estimates to the scoring engine 404 or the requesting entity (e.g., the laptop 108 or the tablet 126). The scoring engine 404 is used to simulate the requesting entity using API messaging such as RESTful API requests 405a to simulate requests 405b for waiting time, and RESTful API responses 405c to simulate the delivery 405d of waiting time estimates 128. The scoring module 402 is used to facilitate this messaging and manage the machine learning model 121 such that the machine learning training module 400 can operate within the system 100.

The machine learning training module 400 includes a database of training data 406 that stores prescriptions 407, store information, and waiting times 408 at which the prescriptions 407 were filled on any number or type(s) of non-transitory computer- or machine-readable storage medium or disk using any number or type(s) of data structures.

As used herein, a non-transitory computer- or machine-readable storage medium or disk may be, but is not limited to, one or more of a hard disk drive (HDD), an optical storage drive, a solid-state storage device, a solid-state drive (SSD), a read-only memory (ROM), a random-access memory (RAM), a compact disc (CD), a compact disc read-only memory (CD-ROM), a digital versatile disk (DVD), a Blu-ray disk, a cache, a flash memory, or any other storage device or storage disk in which information may be stored for any duration (e.g., permanently, for an extended time period, for a brief instance, for temporarily buffering, for caching of the information, etc.).

Input vectors 122 are formed for the prescriptions 407 and passed through the machine learning engine 403 to form test estimated waiting times 410. In the illustrated example of FIG. 4, the developing machine learning model within the machine learning engine 403 is trained using supervised learning. Accordingly, a testing module 412, which may be, or include a portion of a memory unit (e.g., the program memory 602 of FIG. 6) configured to store software, and machine- or computer-readable instructions that, when executed by a processing unit (e.g., the processor 604 of FIG. 6), cause the testing module 412 to compare the test estimated waiting times 410 determined by the machine learning engine 403 for the prescriptions 406 with the actual fill times 408 for the prescriptions 407 to form errors 414 that are used to develop and update the machine learning engine 403. The machine learning engine 403 develops, deploys and updates the final machine learning model 121 using, for example, gradient boosting machine learning, for example, using the open source extreme gradient boosting (xgboost) algorithm, an efficient gradient boosting (lightgbm) algorithm, a neural network, deep learning, a regression technique, etc.

To validate the developing machine learning model within the machine learning engine 403, the training module 401 includes a model validation module 416. The model validation module 416 may be, or include a portion of a memory unit (e.g., the program memory 602 of FIG. 6) configured to store software, and machine- or computer-readable instructions that, when executed by a processing unit (e.g., the processor 604 of FIG. 6), cause the model validation module 416 to statistically validate the developing machine learning model using k-fold cross-validation. The data 406 is randomly split into k parts. The developing machine learning model is trained using k−1 of the k parts of the data 406 which represent prescription characteristics and actual fill times for the prescriptions 407. The machine learning module 120 is evaluated using the remaining one part of the data 406 which represent prescription characteristics and actual fill times for prescriptions 418, which the machine learning engine 403 has not been exposed to. Outputs 420 of the developing machine learning model for the prescriptions 418 are compared to actual fill times 422 for the prescriptions 418 by the model validation module 416 to determine the performance or convergence of developing machine learning model. Performance or convergence can be determined by, for example, identifying when a metric computed over the errors 414 (e.g., a mean-square metric, a rate-of-decrease metric, etc.) satisfies a criteria (e.g., a metric is less than a predetermined threshold, such as a root mean squared error).

In some examples, the developing machine learning model within the machine learning engine 403 is initially trained using historical prescription and fill time data. The machine learning engine 403 may then deploy one or more new or updated machine learning models as new prescriptions are filled. For example, deploying a machine learning model 121 running in parallel with the machine learning engine 403 can be used to estimate waiting times for live prescription waiting time estimate requests. Periodically or nonperiodically, the machine learning model 121 can be updated from the parallel machine learning engine 403. In addition, for example, the machine learning model 121 can be deployed as one or more MLeap model formats to perform scoring within the scoring module 402 and can provide these waiting time estimates 128 in the form of predictions. MLeap is an open source serialization format and execution engine for machine learning pipelines, and the MLeap format enables production and scaling on a Docker container, Kubernetes cluster, etc. Similarly, predictions could be recorded and compared with post-training results to improve the waiting time estimate prediction. Other deployable model formats may include PMML, ONNX, PFA, pickle, etc.

Figure 5:
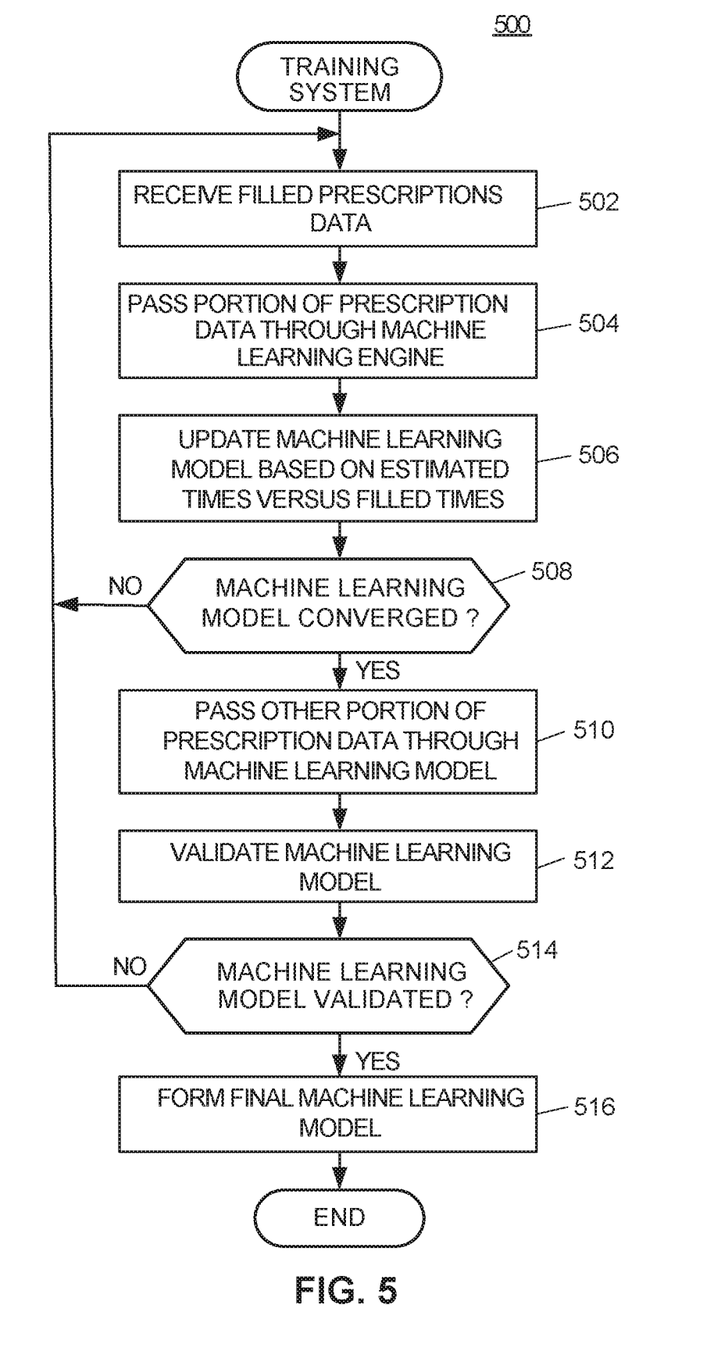
FIG. 5 is a flowchart representative of example methods, hardware logic and instructions for training the machine learning model of FIG. 1.

A flowchart 500 representative of example processes, methods, software, firmware, and computer- or machine-readable instructions for implementing the machine learning training module 400 is shown in FIG. 5. The processes, methods, software and instructions may be an executable program or portion of an executable program for execution by a processor such as the processor 604 of FIG. 6. The program may be embodied in software or instructions stored on a non-transitory computer- or machine-readable storage medium or disk associated with the processor 604. Further, although the example program is described with reference to the flowchart illustrated in FIG. 5, many other methods of implementing the example machine learning training module 400 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an ASIC, a PLD, an FPGA, an FPLD, a logic circuit, etc.) structured to perform the corresponding operation without executing software or firmware.

The example process of FIG. 5 begins with receiving prescriptions and storing them in the training data database 406 (block 502). Prescription characteristics for the prescriptions 407 included in the k−1 of k portions of the data 406 are passed through the machine learning engine 403 (block 504), and the developing machine learning model within the machine learning engine 403 is updated based on comparisons by the testing module 412 of the outputs 410 of the developing machine learning model and fill times for the prescriptions 407 of the k−1 portions of the data 406 (block 506). If training of the developing machine learning model has not converged (block 508), control returns to block 504 to continue training the developing machine learning model. If training of the developing machine learning model has converged (block 508), prescription characteristics for the prescriptions 418 of the remaining portion of the data 406 are passed through the machine learning engine 403 (block 510), and outputs 420 of the developing machine learning model are used by the model validation module 416 to validate the developing machine learning model (block 512). If the developing machine learning model validates (block 514), the machine learning engine 403 is used to form the final machine learning model 121 (block 516) (e.g., coefficients are copied, etc.), and control exits from the example process of FIG. 5. Otherwise, if the developing machine learning model does not validate (block 514), then control returns to block 502 to continue training.

Referring now to FIG. 6, a block diagram of an example computing system 600 to estimate prescription waiting times in accordance with described embodiments is shown. The example computing system 600 may be used to, for example, implement the prescription filler 102, the order handler module 112, the waiting time estimation module 118, the machine learning module 120, and the UI 130. The computing system 600 may also be used to, for example, implement the machine learning training module 400, the training module 401, the scoring module 402, the machine learning engine 403, the testing module 412, the model validation module 416, and the scoring engine 404.

The computing system 600 includes a program memory 602, a processor 604, a RAM 606, and an I/O circuit 608, all of which are interconnected via an address/data bus 610. The program memory 602 may store software, and machine- or computer-readable instructions, which may be executed by the processor 604.

It should be appreciated that although FIG. 6 depicts only one processor 604, the computing system 600 may include multiple processors 604. Example processors 604 include a programmable processor, a programmable controller, a GPU, a DSP, an ASIC, a PLD, an FPGA, an FPLD, etc.

It should be appreciated that although FIG. 6 depicts only one processor 604, the computing system 600 may include multiple nodes (computers) comprising of multiple processors 604, program memories 602, RAM 606 and databases 612 and I/O 608 in the form of computing clusters where a cluster is in the form or one or more of these nodes. Software running these clusters can be Apache® Spark, Dask Python, Apache® Flink, Hadoop® MapReduce®, H20, etc.

Similarly, the program memory 602 may include memories, for example, one or more RAMs (e.g., a RAM 614) or one or more program memories (e.g., a ROM 616), or a cache (not shown) storing one or more corresponding software, and machine- or computer-instructions. For example, the program memory 602 stores software, and machine- or computer-readable instructions, or computer-executable instructions that may be executed by the processor 604 to implement the prescription filler 102, the order handler module 112, the waiting time estimation module 118, the machine learning module 120, and the UI 130; and may also be used to implement the machine learning training module 400, the training module 401, the scoring module 402, the machine learning engine 403, the testing module 412, the model validation module 416, and the scoring engine 404 to estimate prescription waiting times. The software, machine-readable instructions, or computer-executable instructions may be stored on separate non-transitory computer- or machine-readable storage mediums or disks, or at different physical locations.

In some embodiments, the processor 604 may also include, or otherwise be communicatively connected to, a database 612 or other data storage mechanism (one or more hard disk drives, optical storage drives, solid state storage devices, CDs, CD-ROMs, DVDs, blu-ray disks, etc.). In some examples, the database 612 stores the training data database 406.

Although FIG. 6 depicts the I/O circuit 608 as a single block, the I/O circuit 608 may include a number of different types of I/O circuits or components that enable the processor 604 to communicate with peripheral I/O devices. The peripheral I/O devices may be any desired type of I/O device such as a keyboard, a display (a liquid crystal display (LCD), a cathode ray tube (CRT) display, touch, etc.), a navigation device (a mouse, a trackball, a capacitive touch pad, a joystick, etc.), a speaker, a microphone, a button, a communication interface, an antenna, etc.

The I/O circuit 608 may include a number of different network transceivers 618 that enable the computing system 600 to communicate with another computer system via, e.g., a network (e.g., the communication network 130). The network transceiver 618 may be a Wi-Fi transceiver, a Bluetooth® transceiver, an infrared transceiver, a cellular transceiver, an Ethernet network transceiver, an asynchronous transfer mode (ATM) network transceiver, a digital subscriber line (DSL) modem, a cable modem, etc.

The program memory 602, the RAM(s) 606, 614 and the ROM(s) 616 may be implemented in any known form of volatile or non-volatile computer storage media, including but not limited to, semiconductor memories, magnetically readable memories, and/or optically readable memories, for example, but does not include carrier waves.

Figure 7A:
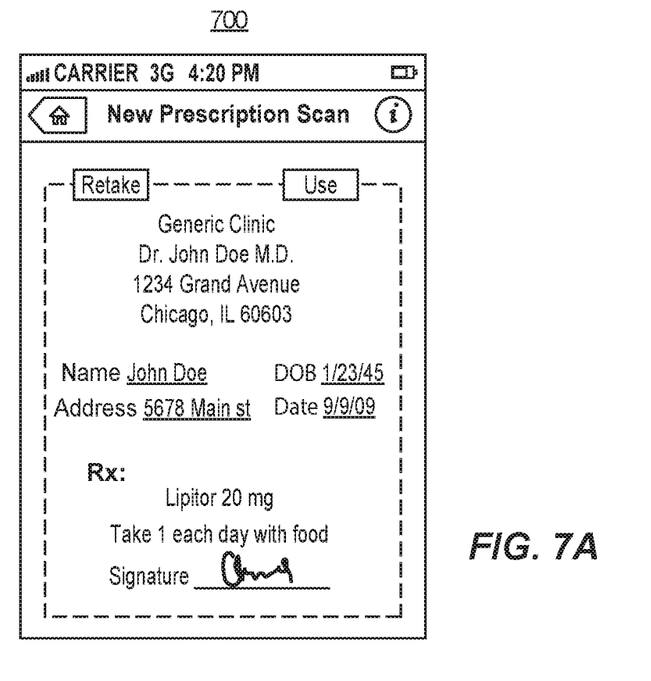
FIG. 7A is an example prescription scan screen of a client application executed on a client device.

As described above, the patient may scan an image of the prescription via a client application executed on the patient's client device. The client application may transmit the prescription image to the prescription filler 102, which may in turn, provide an indication of the estimated waiting time for filling the prescription on a display of the patient's client device. FIG. 7A illustrates an example prescription scan screen 700 of a client application executed on a client device. The client device may be the patient's client device, a pharmacy workstation, or any other suitable client device. The prescription scan screen 700 may include an image capture area and a user control (not shown) which may activate a camera in the client device to capture an image of the prescription. The prescription scan screen 700 may also include a user control, such as a "Use" button for transmitting the prescription image to the prescription filler 102. In some embodiments, the client application may include a user control for the patient to select a retail pharmacy location for filling the prescription which may also be transmitted to the prescription filler 102.

Figure 7B:
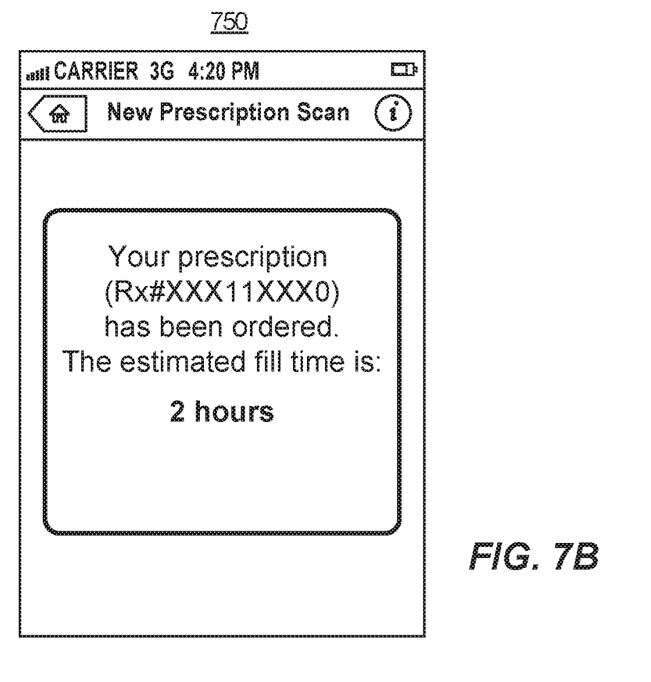
FIG. 7B is an example prescription wait time estimation screen of a client application executed on a client device.

Also in some embodiments, the client application may include a user control for the patient to request an estimated waiting time for the prescription. In other embodiments, the prescription filler 102 may automatically determine an estimated waiting time for the prescription upon receiving a prescription and may transmit an indication of the estimated waiting for the prescription to the patient's client device, a pharmacy workstation for the retail pharmacy filling the prescription, or any other suitable client device. The prescription filler 102 may transmit the indication of the estimated waiting time via email, text message, push notification, the client application, a website, etc. FIG. 7B illustrates an example prescription wait time estimation screen 750 of a client application executed on a client device. The prescription wait time estimation screen 750 may include an indication of the estimated waiting time for the prescription (e.g., two hours), and identification information for the prescription (e.g., Rx #XXX11XXX0).

In some embodiments, when the estimated waiting time is shorter at an alternative retail pharmacy location within a threshold distance of the retail pharmacy location, the prescription wait time estimation screen 750 may include an indication of the estimated waiting time at the alternative retail pharmacy location and a recommendation for the patient to request that the prescription is filled at the alternative retail pharmacy location. Also in some embodiments, when the estimated waiting time may be reduced by having the patient contact the prescriber, the prescription wait time estimation screen 750 may include a recommendation for the patient to contact the prescriber and/or an indication of the estimated waiting time if the patient contacts the prescriber.

The prescription wait time estimation screen 750 may also include a user control (not shown) for requesting to fill the prescription in response to receiving the estimated waiting time. For example, if the patient is satisfied with the estimated waiting time, the patient may select the user control and the request may be transmitted to the prescription filler 102. In turn, the prescription filler 102 may provide instructions to the fulfillment system 116 to prepare the prescription for delivery to the patient. If the patient is not satisfied with the estimated waiting time, the patient may contact the prescriber or may select a different retail pharmacy location, such as an alternative retail pharmacy location having a shorter estimated waiting time. Then the patient may request to fill the prescription, via the user control, at the alternative retail pharmacy location.

Some examples may be described using "coupled" or "connected" along with their derivatives. For example, some examples may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Unless specifically stated otherwise, "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

As used herein, the terms "comprises," "comprising," "includes," "including," "has," "having" or any other variation thereof, are intended to cover a non-exclusive inclusion. Thus, whenever a claim employs any form of "include" or "comprise" (e.g., comprises, includes, comprising, including, having, etc.) As a preamble or within a claim recitation of any kind, it is to be understood that additional elements, terms, etc. May be present without falling outside the scope of the corresponding claim or recitation. As used herein, when the phrase "at least" is used as the transition term in, for example, a preamble of a claim, it is open-ended in the same manner as the term "comprising" and "including" are open ended.

Further, unless expressly stated to the contrary, "or" refers to an inclusive or and not to an exclusive or. For example, a, b or c refers to any combination or subset of a, b, c such as (1) a alone, (2) b alone, (3) c alone, (4) a with b, (5) a with c, (6) b with c, and (7) a with b and with c. As used herein, the phrase "at least one of a and b" is intended to refer to implementations including any of (1) at least one a, (2) at least one b, and (3) at least one a and at least one b. Similarly, the phrase "at least one of a or b" is intended to refer to implementations including any of (1) at least one a, (2) at least one b, and (3) at least one a and at least one b.

As used herein, the expressions "in communication," "coupled" and "connected, including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, the term non-transitory computer-readable medium is expressly defined to include any type of computer-readable storage device and/or storage disk and to exclude propagating signals and to exclude transmission media. As used herein, the term non-transitory machine-readable medium is expressly defined to include any type of machine-readable storage device and/or storage disk and to exclude propagating signals and to exclude transmission media.

Any references, including publications, patent applications, and patents cited herein are hereby incorporated in their entirety by reference to the same extent as if each reference were individually and specifically indicated to be incorporated by reference and were set forth in its entirety herein.

Finally, unless a claim element is defined by reciting the word "means" and a function without the recital of any structure, it is not intended that the scope of any claim element be interpreted based on the application of 35 U.S.C. § 112, sixth paragraph.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computer-implemented method, executed by a processor, to estimate the waiting time for filling a prescription medication for a patient, the method comprising:
    training, by a processor, a machine learning model to predict an estimated waiting time for filling the prescription medication for the patient using, for each of a plurality of previously filled prescriptions, (i) a set of characteristics of each previously filled prescription, and (ii) a fill time for each previously filled prescription,
        wherein the set of characteristics of each previously filled prescription includes at least one of: prescription information, medication information, usage information, pharmacy stock information, a number of patients currently waiting for a prescription medication to be filled, or a number of prescriptions waiting to be filled;
    receiving, with a processor, a prescription for a medication for a patient;
    receiving, with the processor, a request for an estimated waiting time for filling the prescription medication for the patient;
    identifying, by the processor, a set of characteristics of the prescription medication for the patient;
    applying, by the processor, the set of characteristics of the prescription medication to the machine learning model to predict the estimated waiting time for filling the prescription medication for the patient; and
    providing, by the processor, an indication of the estimated waiting time for display on a client device.

2. The method of claim 1, further comprising:
    determining, by the processor, whether to contact the prescriber to decrease the estimated waiting time; and
    in response to determining that contacting the prescriber decreases the estimated waiting time, providing, by the processor, a recommendation to the patient to contact the prescriber for display on the client device, wherein the recommendation includes an estimated amount of waiting time saved by contacting the prescriber.

3. The method of claim 2, further comprising:
    determining, by the processor, that the prescription has not been filled and that the expected amount of waiting time has been exceeded; and
    providing, by the processor, an automatic attempt to contact the prescriber.

4. The method of claim 1, further comprising:
    receiving, with the processor, a requested pharmacy location for retrieving the prescription medication for the patient.

5. The method of claim 4, further comprising:
    identifying, by the processor, a set of characteristics of the requested pharmacy location; and
    applying, by the processor, the set of characteristics of the requested pharmacy location to the machine learning model to determine the estimated waiting time for filling the prescription medication for the patient.

6. The method of claim 4, further comprising:
    identifying, by the processor, one or more alternative pharmacy locations within a threshold distance of the requested pharmacy location;
    for each of the one or more alternative pharmacy locations:
        identifying, by the processor, a set of characteristics of the alternative pharmacy location; and
        applying, by the processor, the set of characteristics of the alternative pharmacy location to the machine learning model to determine the estimated waiting time for filling the prescription medication for the patient; and
    providing, by the processor, an indication of one of the one or more alternative pharmacy locations which has a shorter estimated waiting time than the estimated waiting time for filling the prescription medication at the requested pharmacy location for display on the client device.

7. The method of claim 1, wherein the prescription is received from the patient.

8. The method of claim 1, further comprising receiving, from the client device in response to the providing of the estimated waiting time, a request to fulfill the prescription.

9. The method of claim 1, wherein training the machine learning model includes applying gradient boosting.

10. The method of claim 1, further comprising:
    training the machine learning model with data from a first subset of the plurality of previously filled prescriptions; and
    validating the machine learning model with data from a second subset of the plurality of previously filled prescriptions.

11. A non-transitory computer-readable storage medium comprising instructions that, when executed, cause a processor to:
    train a machine learning model to predict an estimated waiting time for filling a prescription medication for a patient using, for each of a plurality of previously filled prescriptions, (i) a set of characteristics of each previously filled prescription, and (ii) a fill time for each previously filled prescription,
        wherein the set of characteristics of each previously filled prescription includes at least one of: prescription information, medication information, usage information, pharmacy stock information, a number of patients currently waiting for a prescription medication to be filled, or a number of prescriptions waiting to be filled;

receive a prescription for a medication for a patient;

receive a request for an estimated waiting time for filling the prescription medication for the patient;

identify a set of characteristics of the prescription medication for the patient;

apply the set of characteristics of the prescription medication to the machine learning model to predict the estimated waiting time for filling the prescription medication for the patient; and provide an indication of the estimated waiting time for display for filling the prescription medication for the patient on a client device.

12. The non-transitory computer-readable storage medium of claim 11, wherein the instructions further cause the processor to:

determine whether to contact the prescriber to decrease the estimated waiting time; and in response to determining that contacting the prescriber decreases the estimated waiting time, provide a recommendation to the patient to contact the prescriber for display on the client device, wherein the recommendation includes an estimated amount of waiting time saved by contacting the prescriber.

13. The non-transitory computer-readable storage medium of claim 11, wherein the instructions further cause the processor to:

receive a requested pharmacy location for retrieving the prescription medication for the patient.

14. The non-transitory computer-readable storage medium of claim 13, wherein the instructions further cause the processor to:

identify a set of characteristics of the requested pharmacy location; and apply the set of characteristics of the requested pharmacy location to the machine learning model to determine the estimated waiting time for filling the prescription medication for the patient.

15. The non-transitory computer-readable storage medium of claim 14, wherein the instructions further cause the processor to:

identify one or more alternative pharmacy locations within a threshold distance of the requested pharmacy location;

for each of the one or more alternative pharmacy locations:

identify a set of characteristics of the alternative pharmacy location; and apply the set of characteristics of the alternative pharmacy location to the machine learning model to determine the estimated waiting time for filling the prescription medication for the patient; and provide an indication of one of the one or more alternative pharmacy locations which has a shorter estimated waiting time than the estimated waiting time for filling the prescription medication at the requested pharmacy location for display on the client device.

16. The non-transitory computer-readable storage medium of claim 11, wherein the prescription is received from the patient.

17. The non-transitory computer-readable storage medium of claim 11, wherein the instructions further cause the processor to:

receive, from the client device in response to the providing of the estimated waiting time, a request to fulfill the prescription.

18. The non-transitory computer-readable storage medium of claim 11, wherein the instructions further cause the processor to:

train the machine learning model with data from a first subset of the plurality of previously filled prescriptions; and validate the machine learning model with data from a second subset of the plurality of previously filled prescriptions.

* * * * *